United States Patent [19]

Campbell et al.

[11] Patent Number: 4,533,762

[45] Date of Patent: Aug. 6, 1985

[54] PREPARATION OF CHLOROTRIFLUOROETHYLENE TELOMERS WITH BISFLUOROXYDIFLUOROMETHANE

[75] Inventors: Donald H. Campbell, Niagara-on-the-Lake, Canada; Michael J. Fifolt; Mohan S. Saran, both of Grand Island, N.Y.

[73] Assignee: Occidental Chemical Corporation, Niagara Falls, N.Y.

[21] Appl. No.: 545,018

[22] Filed: Oct. 24, 1983

[51] Int. Cl.³ .................... C07C 179/00; C07C 43/00
[52] U.S. Cl. .................................. 568/677; 568/683; 570/139
[58] Field of Search .................. 570/139, 142, 138; 568/300, 677, 683; 562/605

[56] References Cited

U.S. PATENT DOCUMENTS

| | | | |
|---|---|---|---|
| 2,757,167 | 7/1956 | Cook | 570/138 |
| 2,875,253 | 2/1959 | Barnhart | 570/139 |
| 2,885,448 | 5/1959 | Miller | 570/139 |
| 2,950,300 | 8/1960 | Brandon | 570/138 |
| 4,030,994 | 6/1977 | Kollonitsch | 562/605 |

*Primary Examiner*—Charles F. Warren
*Assistant Examiner*—Joseph A. Boska
*Attorney, Agent, or Firm*—James F. Tao; William G. Gosz

[57] ABSTRACT

A telomerization process comprises reacting chlorotrifluoroethylene with bisfluoroxydifluoromethane. The telomerization reaction is conducted in either liquid chlorotrifluoroethylene without a solvent or in solution. The telomers thus formed can optionally be fluorinated by reaction with a suitable fluorinating agent to improve their stability.

8 Claims, No Drawings

PREPARATION OF CHLOROTRIFLUOROETHYLENE TELOMERS WITH BISFLUOROXYDIFLUOROMETHANE

BACKGROUND OF THE INVENTION

The present invention relates to the reaction of chlorotrifluoroethylene, hereinafter designated as "CTFE", with bisfluoroxydifluoromethane, hereinafter designated as "BDM", to produce highly fluorinated telomers. The telomers thus formed hve properties which distinguish them from other CTFE telomers and make them commercially attractive products. Such properties include superior solvent characteristics which are useful in formulating non-flammable hydraulic fluids.

Various methods of preparing telomers from CTFE are known in the prior art and have been practiced commercially for many years.

An article by William T. Miller, Jr. et al in *Industrial and Engineering Chemistry*, pages 333–337 (1947), entitled "Low Polymers of Chlorotrifluoroethylene", describes a process for producing low molecular weight polymers of CTFE by carrying out the polymerization in a solution of chloroform using benzoyl peroxides as polymerization promoters. Other solvents disclosed in the reference as being useful for this purpose include carbon tetrachloride and tetrachloroethylene. The solution is heated in a pressure vessel for $1\frac{3}{4}$ hours at 100° C., and the unreacted CTFE monomer and chloroform are removed by distillation, leaving a "crude" telomer of general formula $CHCl_2(CF_2CClF)_nCl$, which can be further heated and distilled to yield products ranging from a light oil to a semi-solid wax or grease. In this formula, n designates the chain length (the number of repeating units in the telomer chain), and is in the range of 1 to 20.

A more recent development in this field is described in a series of articles by Y. Pietrasanta et al entitled "Telomerization by Redox Catalysis" appearing in the *European Polymer Journal*, Vol. 12 (1976). This technology involves the reaction of a chlorinated telogen, such as carbon tetrachloride, with CTFE in the presence of benzoin and a suitable redox catalyst, such as ferric chloride hexahydrate ($FeCl_3.6H_2O$). The telomerization reaction is suitably carried out in acetonitrile which is a common solvent for the reactants and catalysts. The telomerization reaction can be illustrated as follows, wherein n is as defined above:

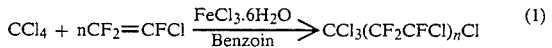

$$CCl_4 + nCF_2=CFCl \xrightarrow[\text{Benzoin}]{FeCl_3.6H_2O} CCl_3(CF_2CFCl)_nCl \quad (1)$$

The telomers produced according to the above-described process have end groups containing chlorine atoms. When used in a particular application, especially high temperature or corrosive applications, the chlorine atoms can be hydrolyzed, which may result in cleavage of the telomer and a loss of physical properties of the fluid. In order to prevent such a condition, the end groups are stabilized by fluorinating the telomer to replace some or all of the chlorine atoms with fluorine. The fluorine atoms form a stronger bond with carbon and are less prone to cleavage. This results in a fluid which has superior performance over a wider range of operating conditions.

Fluorination of the telomer is accomplished by reaction with a suitable fluorinating gent, such as chlorine trifluoride or hydrogen fluoride. However, fluorination involves an additional process step which increases processing costs. It would be desirable to reduce the amount of fluorination required or eliminate this procedure in its entirety. It would also be desirable to develop superior telomers having improved physical characteristics, such as better solvent properties. These are the primary objectives of the present invention.

SUMMARY OF THE INVENTION

The present invention relates to a process for preparing telomers by reacting chlorotrifluoroethylene with bisfluoroxydifluormethane. The reaction can be conducted in liquid chlorotrifluoroethylene without a solvent at a temperature preferably below the boiling point of chlorotrifluoroethylene ($-30°$ C.). Alternatively, the reaction can be conducted in a suitble solvent at somewhat higher temperatures if desired.

The telomers produced by this process have improved physical properties as compared to telomers produced by reacting chlorotrifluoroethylene with carbon tetrachloride, or some equivalent telogen, as starting materials.

DESCRIPTION OF THE PREFERRED EMBODIMENTS

According to the present invention, chlorotrifluoroethylene is reacted with bisfluoroxydifluoromethane in liquid CTFE or in solution. If the reaction is conducted in liquid CTFE, a temperature below the boiling point of CTFE, i.e. about $-30°$ C., should be maintained. If high pressure conditions are used, the reaction temperature can be increased to about 100° C. An operable temperature range is therefore from about 100° C. to about $-100°$ C. The absence of a solvent generally entails the use of lower temperatures than a solution telomerization process, but avoids the necessity of separation and purification of the product.

Alternatively, the reaction can be conducted in solution using a solvent which is inert to fluorine under the reaction conditions. Suitable solvents are generally fluorinted and include, but are not limited to, fluorotrichloromethane, trifluoroacetic acid, trichlorotrifluoroethane, and the like. Of these solvents, fluorotrichloromethane is preferred. The solution temperature is preferably maintained in the range of from about $-100°$ C. to about 100° C. during the reaction.

The telomerization reaction can be carried out in a stirred reactor at the indicated temperature conditions and produces a complex mixture of telomers.

The reaction of CTFE with BDM may produce telomers which contain some hydrolyzable chlorine. In this event, it is necessary to fluorinate the telomers to replace the chlorine with fluorine. This results in a product having improved stability and non-reactivity. Chlorine trifluoride ($ClF_3$) is a suitable fluorinating agent for this purpose, although other fluorinating agents such as hydrogen fluoride can be used. The amount of such fluorination required, however, is less than for other CTFE telomers.

Bisfluoroxydifluoromethane, which is a starting material in this invention, is a known compound. However, this compound is not readily available in regular channels of commerce. A convenient and inexpensive technique for producing BDM which has been reported in the literature is the reaction of carbon dioxide with fluorine in the presence of a metal fluoride such as cesium fluoride. See, for example, F. A. Hohorst and J. M.

Shreeve, *Inorganic Synthesis*, Vol. 11, pages 143–147 (1968), and *Journal of the American Chemical Society*, Vol. 89, pages 1809–10 (1967). This reaction proceeds as follows, wherein M designates a suitable metal such as cesium:

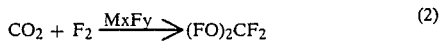

$$CO_2 + F_2 \xrightarrow{M_xF_y} (FO)_2CF_2 \quad (2)$$

The telomers prepared according to this invention can be used in a variety of applications, such as fluids for hydraulic systems, pumps and instruments. In such applications, various additives may be used to modify the physical properties of the telomers. In addition to their inherent non-flammability and corrosion resistance, the telomers of this invention have been found to possess excellent solvent properties in comparison to other CTFE-derived fluids.

The following example is intended to further illustrate the various embodiments and advantages of the present invention without limiting it thereby.

EXAMPLE

Five (5) grams of chlorotrifluoroethylene and 50 ml. of fluorotrichloromethane were placed in a 50 ml., three-neck, round bottom flask. The flask was equipped with a low temperature thermometer, a gas inlet tube, a gas outlet tube connected to an aqueous potassium iodide-acetic acid trap, and a magnetic stirring bar. The solution was cooled to −37° C. and BDM was added at a rate of 0.36 grams/hr. for two hours. The solvent was removed under reduced pressure yielding 0.5 grams of telomers as determined by GC analysis.

While various embodiments and exemplifications of this invention have been shown and described in the specification, modifications and variations thereof will be readily appreciated by those skilled in the art. It is to be understood, therefore, that the appended claims are intended to cover all such modifications and variations which are considered to be within the scope and spirit of the present invention.

What is claimed is:

1. A process for producing telomers consisting essentially of reacting chlorotrifluoroethylene with bis-fluoroxydifluoromethane.

2. The process of claim 1 which is conducted in liquid CTFE without a solvent.

3. The process of claim 2 which is conducted at a temperature of less than about −30° C.

4. The process of claim 2 which is conducted at a temperature in the range of from about 100° C. to about −100° C.

5. A process for producing telomers consisting essentially of reacting chlorotrifluoroethylene with bis-fluoroxydifluoromethane in a solvent.

6. The process of claim 5 wherein the solvent is selected from the group consisting of fluorotrichloromethane, trifluoroacetic acid and trichlorotrifluoroethane.

7. The process of claim 6 wherein the solvent is fluorotrichloromethane.

8. The process of claim 5 which is conducted at a temperature of from about −100° C. to about 100° C.

* * * * *